United States Patent [19]

Crow et al.

[11] Patent Number: 6,054,486
[45] Date of Patent: Apr. 25, 2000

[54] USE OF 9-DEOXY-2',9-α-METHANO-3-OXA-4, 5,6-TRINOR-3,7-(1',3'-INTERPHENYLENE)-13, 14-DIHYDRO-PROSTAGLANDIN $F_1$ TO TREAT PERIPHERAL VASCULAR DISEASE

[75] Inventors: James W. Crow, Chapel Hill; Shelmer D. Blackburn, Jr., Raleigh; Robert Roscigno, Chapel Hill; Michael Wade, Mebane; Gilles Cloutier, Chapel Hill, all of N.C.; Martine Rothblatt, Silver Spring, Md.

[73] Assignee: United Technology Corporation, Washington, D.C.

[21] Appl. No.: 09/190,450

[22] Filed: Nov. 13, 1998

Related U.S. Application Data

[60] Provisional application No. 60/066,049, Nov. 14, 1997.

[51] Int. Cl.⁷ ..................................................... A61R 31/19
[52] U.S. Cl. ................................................................. 514/571
[58] Field of Search .............................................. 514/571

[56] References Cited

U.S. PATENT DOCUMENTS

| | | | |
|---|---|---|---|
| 4,306,075 | 12/1981 | Aristoff | 560/56 |
| 4,490,537 | 12/1984 | Johnson . | |
| 4,499,085 | 2/1985 | Masuda . | |
| 5,153,222 | 10/1992 | Tadepalli et al. | 514/571 |
| 5,814,301 | 9/1998 | Klopp et al. . | |

FOREIGN PATENT DOCUMENTS

| | | |
|---|---|---|
| 1236380 | 7/1996 | U.S.S.R. . |
| 83 04021 | 11/1983 | WIPO . |

OTHER PUBLICATIONS

Y. Okuda et al. Prostaglandins, vol. 52 "Acute Effect of Beraprost Sodium on Lower Limb Circulation in Patients with Non–Insulin–Dependent Diabetes Melitus–Evaluation . . . Ultrasonography," pp. 375–384 (Nov. 1996).

Patterson et al. The American Journal of Cardiology, vol. 75, "Acute Hemodynamic Effects of the Prostacyclin Analog 15AU81 in Service Congestive Heart failure," pp. 26A–33A (Jan. 1995).

Mohler, Emile R. "Medical Management of Claudication," pp. 1–6, (Mar. 1997).

Mohler, Emile R. "Clinical Manifestations of Claudication," pp. 1–4 (Sep. 1996).

Neschis et al. "Surgical Indications for the Patient with Limb Threatening Ischemia," pp. 1–10.

Belch et al. Circulation, vol. 95, No. 9, "Randomized, Double–Blind, Placebo–Controlled Study Evaluating the the Efficacy and Safety of AS–013 . . . With Intermittent Claudication," pp. 2298–2301 (May, 1997).

*Primary Examiner*—James H. Reamer
*Attorney, Agent, or Firm*—Foley & Lardner

[57] ABSTRACT

An improved treatment for peripheral vascular disease is described using 9-deoxy-2',9-α-methano-3-oxa-4,5,6-trinor-3,7-(1',3'-interphenylene)-13,14-dihydro-prostaglandin $F_1$.

17 Claims, No Drawings

USE OF 9-DEOXY-2',9-α-METHANO-3-OXA-4, 5,6-TRINOR-3,7-(1',3'-INTERPHENYLENE)-13, 14-DIHYDRO-PROSTAGLANDIN $F_1$ TO TREAT PERIPHERAL VASCULAR DISEASE

This application claims the benefit under Title 35, United States Code § 119(e) of U.S. provisional Ser. No. 60/066,049, filed Nov. 14, 1997.

FIELD

The invention relates to the use of 9-deoxy-2',9-α-methano-3-oxa-4,5,6-trinor-3,7-(1',3'-interphenylene)-13,14-dihydro-prostaglandin $F_1$ (hereafter "UT-15") to treat peripheral vascular disease and kits for this purpose.

BACKGROUND

The compound UT-15 is a known compound disclosed in U.S. Pat. No. 4,306,075 in example 33. UT-15 is a synthetic analog of epoprostenol, a prostaglandin $F_1$. The activities ascribed to the various compounds of this patent include inhibition of platelet aggregation, reduction of gastric secretion, and bronchodilation. It is indicated that the compounds of this patent have useful application as anti-thrombotic agents, anti-ulcer agents, and anti-asthma agents.

U.S. Pat. No. 5,153,222 discloses the use of UT-15 and related compounds to treat pulmonary hypertension.

Prostaglandin $E_1$ has been found to increase walking distance in a small but statistically significant group of patients with peripheral arterial occlusive disease. However, since this drug is rapidly inactivated in the lungs, it must be administered intra-arterially, which leads to numerous harmful side effects. See Belch et al., *Circulation*, 95(9): 2298–2302 (1997). Belch further discloses the use of AS-013, a prostaglandin $E_1$ prodrug, to treat peripheral arterial occlusive disease, presenting as intermittent claudication.

Okuda et al., *Prostaglandins*, 52(5): 375–384 (November 1996) showed that beraprost sodium, a stable analogue of prostaglandin $I_2$, increased the cross-sectional area and the blood flow index of the dorsal pedis artery in non-insulin dependent diabetes patients. In addition, Okuda showed an increase in the dermal microcirculatory blood volume of these patients.

Patterson et al., *Amer. J. of Cardiology*, 75(1995): 26A–33A, have shown the vasodilator effects of UT-15 in patients with class III or class IV heart failure.

SUMMARY

The present inventors discovered that UT-15 is especially well suited for the treatment of peripheral vascular disease compared to other prostaglandin-type compounds because it is not degraded when it passes through the lungs, it has a long biological half-life, it has potent peripheral vasodilatory properties, it is a highly potent platelet aggregation inhibitor, and it inhibits the release of vasoconstrictive substances.

Accordingly, it is an object of the present invention to provide an improved treatment for peripheral vascular disease comprising administering to a subject in need thereof an effective amount of UT-15 and pharmaceutically acceptable salts and acid derivatives thereof, as well as kits for accomplishing this purpose.

DETAILED DESCRIPTION

The present invention relates to a method for treatment of peripheral vascular disease, including peripheral arterial occlusive disease and intermittent claudication, comprising administering to a subject, preferably a human being, in need thereof an effective amount of UT-15 and/or its pharmaceutically acceptable salts and acid derivatives thereof.

The present invention also relates to kits for accomplishing such treatment comprising (i) an effective amount of UT-15, its pharmaceutically acceptable salts, and/or acid derivatives thereof, (ii) one or more pharmaceutically acceptable carriers and/or additives, and (iii) instructions for use in treating peripheral vascular disease.

As used herein, the phrase "instructions for use" shall mean any FDA-mandated labelling, instructions, or package inserts that relate to the administration of UT-15 for the purpose of treating peripheral vascular disease. For example, instructions for use may include, but are not limited to, indications for peripheral vascular disease, identification of specific symptoms of peripheral vascular disease that can be ameliorated by UT-15, and recommended dosage amounts for subjects suffering from peripheral vascular disease.

The term "acid derivative" is used herein to describe C1–4 alkyl esters and amides, including amides wherein the nitrogen is optionally substituted by one or two C1–4 alkyl groups.

The invention also includes bioprecursors or "pro-drugs" of UT-15, that is, compounds which are converted in vivo to UT-15 or its pharmaceutically active derivatives thereof.

Further aspects of the present invention are concerned with the use of UT-15, or a pharmaceutically acceptable salt or acid derivative thereof, in the manufacture of a medicament for the treatment of peripheral vascular disease The present invention extends to non-physiologically acceptable salts of UT-15 which may be used in the preparation of the pharmacologically active compounds of the invention. The physiologically acceptable salts of UT-15 include salts derived from bases.

Base salts include ammonium salts, alkali metal salts such as those of sodium and potassium, alkaline earth metal salts such as those of calcium and magnesium, salts with organic bases such as dicyclohexylamine and N-methyl-D-glucamine, and salts with amino acids such as arginine and lysine.

Quaternary ammonium salts can be formed, for example, by reaction with lower alkyl halides, such as methyl, ethyl, propyl, and butyl chlorides, bromides, and iodides, with dialkyl sulphates, with long chain halides, such as decyl, lauryl, myristyl, and stearyl chlorides, bromides, and iodides, and with aralkyl halides, such as benzyl and phenethyl bromides.

The amount of UT-15, or a physiologically acceptable salt or acid derivative thereof, which is required in a medication or diagnostic aid according to the invention to achieve the desired effect will depend on a number of factors, in particular the specific application, the nature of the particular compound used, the mode of administration, and the condition of the patient. In general, a daily dose per patient for the treatment of peripheral vascular disease is in the range 25 μg to 250 mg; typically from 0.5 μg to 2.5 mg, preferably from 7 μg to 285 μg, per day per kilogram bodyweight. For example, an intravenous dose in the range 0.5 μg to 1.5 mg per kilogram bodyweight per day may conveniently be administered as an infusion of from 0.5 ng to 1.0 μg per kilogram bodyweight per minute. A preferred dosage is 10 ng/kg/min. Infusion fluids suitable for this purpose contain, for example, from 10 ng to 10 μg per milliliter. Ampoules for injection contain, for example, from 0.1 μg to 1.0 mg and orally administrable unit dose formulations, such as tablets or capsules, contain, for example, from 0.1 to 100 mg, typically from 1 to 50 mg. For diagnostic purposes, a single unit dose formulation may be administered. In the case of physiologically acceptable salts, the weights indicated above refer to the weight of the active compound ion, that is, the ion derived from UT-15.

In the manufacture of a medicament or diagnostic aid according to the invention, hereinafter referred to as a "formulation", UT-15 and its physiologically acceptable salts and acid derivatives are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.05% to 95% by weight of the active compound. One or more of UT-15 and/or its physiologically acceptable salts or acid derivatives may be incorporated in the formulations of the invention, which may be prepared by any of the well known techniques of pharmacy for admixing the components.

In addition to UT-15, other pharmacologically active substances may be present in the formulations of the present invention which are known to be useful for treating peripheral vascular disease. For example, the compounds of the invention may be present in combination with trental, a substance known to increase red blood cell deformability.

The formulations of the invention include those suitable for oral, inhalation (in solid and liquid forms), rectal, topical, buccal (e.g. sub-lingual), parenteral (e.g. subcutaneous, intramuscular, intradermal, or intravenous) and transdermal administration, although the most suitable route in any given case will depend on the nature and severity of the condition being treated and on the nature of the particular form of UT-15, or the physiologically acceptable salt or acid derivative thereof, which is being used.

Formulations suitable for oral administration may be presented in discrete units, such as capsules, cachets, lozenges, or tablets, each containing a predetermined amount of UT-15 or a physiologically acceptable salt or acid derivative thereof; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients)

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising UT-15, or a physiologically acceptable salt or acid derivative thereof, in a flavored base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of UT-15, or a physiologically acceptable salt or acid derivative thereof, which preparations are preferably isotonic with the blood of the intended recipient. These preparations are preferably administered intravenously, although administration may also be effected by means of subcutaneous, intramuscular, or intradermal injection. Such preparations may conveniently be prepared by admixing the compound with water or a glycine buffer and rendering the resulting solution sterile and isotonic with the blood. Injectable formulations according to the invention generally contain from 0.1 to 5% w/v of active compound and are administered at a rate of 0.1 ml/min/kg.

Formulations suitable for rectal administration are preferably presented as unit dose suppositories. These may be prepared by admixing UT-15, or a physiologically acceptable salt or acid derivative thereof, with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols, and combinations of two or more thereof. The active compound is generally present at a concentration of from 0.1 to 15% w/w, for example, from 0.5 to 2% w/w. Formulations for transdermal administration may be delivered by iontophoresis (see, for example, Pharmaceutical Research 3(6), 318, (1986)) and typically take the form of an optionally buffered aqueous solution of UT-15 or of a salt or acid derivative thereof. Suitable formulations comprise citrate or bis/tris buffer (pH 6) or ethanol/water and contain from 0.1 to 0.2M active ingredient.

The compounds of the present invention are conveniently prepared by methods the same as or analogous to those described in U.S. Pat. No. 4,306,075 and co-pending application Ser. No. 08/957,726 filed on Oct. 24, 1997.

There are three features of UT-15's pharmacological profile in particular which make it well suited for treating peripheral vascular disease. Those features are (1) its vasodilation effect, (2) its inhibition of platelet function, and (3) its cytoprotective effect. In addition to having a potent vasodilation effect, the present inventors believe that one important aspect of an effective treatment for peripheral vascular disease is that the active ingredient should be able to inhibit platelet function, which may be an exacerbating factor in peripheral vascular disease. UT-15 exhibits this pharmacological profile.

Administration Of UT-15 To Humans Suffering From Peripheral Vascular Disease

Eight patients with moderate to severe peripheral vascular disease (Fontaine Stage IIb–III) were dosed with placebo for a minimum of 30 minutes and then with increasing doses of UT-15 (one hour of dosing at each dose step) until the maximum tolerated dose. Safety was assessed by adverse experience monitoring and clinical laboratory tests.

Common side effects at peak dose were expected and included headache and nausea. No serious adverse events were noted during hospitalization. The most common maintenance dosing level was 10 ng/kg/min. Unaudited data summarized below compare blood flow velocity at baseline and the end of the maintenance dosing period, and include all arteries for which data were available at both time points (up to 12 lower limb arteries in each patient). The data show that blood flow velocity was increased significantly. Acute intravenous UT-15 administration was well-tolerated in patients with moderate to severe peripheral vascular disease. Potentially clinically significant improvement in lower limb blood flow was observed when UT-15 was administered actutely at a maximum tolerated dose. The results are presented below in Tables 1 and 2:

TABLE 1

Lower Limb Blood Flow Velocity After Acute Treatment

| Baseline | End of Treatment | % Change from Baseline |
|---|---|---|
| 64 ± 8 | 78 ± 9 | 14 ± 6 (23 ± 9) |

Mean in cm/s ± standard error. N = 8 patients.

TABLE 2

Summary Of Lower Limb Blood Flow Velocity (BFV) Changes After Acute Treatment

| Arteries W/Increase In BFV | Arteries W/Decrease In BFV | p (sign test) |
|---|---|---|
| 56 | 19 | <.0000001 |

Administration Of UT-15 To Anesthetized Dogs

Tests have been performed which support the use of UT-15 to treat peripheral vascular disease. In anesthetized dogs, intravenous boluses (0.32–3.2 µg/kg) and 10-minute infusions of UT-15 produced dose-dependent decreases in mean arterial blood pressure. Also, in anesthetized dogs, intravenous infusions of UT-15 (0.1–3.0 µg/kg/min) for four hours produced dose-dependent decreases in mean total peripheral vascular resistance.

Administration of UT-15 To Anesthetized Piglets

Another set of tests has been performed in anesthetized newborn piglets. Intravenous boluses of UT-15 (6 and 12 µg/kg) were shown to abolish hypoxia-induced increases in pulmonary vascular resistance in anesthetized newborn piglets.

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

What is claimed is:

1. A method for treatment of peripheral vascular disease comprising administering to a subject in need thereof an effective amount of 9-deoxy-2',9-α-methano-3-oxa-4,5,6-trinor-3,7-(1',3'-interphenylene)-13,14-dihydro-prostaglandin $F_1$, its pharmaceutically acceptable salts, and/or acid derivatives thereof.

2. The method as claimed in claim 1, wherein a pharmaceutically acceptable salt of 9-deoxy-2',9-α-methano-3-oxa-4,5,6-trinor-3,7-(1',3'-interphenylene)-13,14-dihydro-prostaglandin $F_1$ is administered.

3. The method as claimed in claim 1, wherein the subject is a human being.

4. The method as claimed in claim 1, wherein the 9-deoxy-2',9-α-methano-3-oxa-4,5,6-trinor-3,7-(1',3'-interphenylene)-13,14-dihydro-prostaglandin $F_1$ is administered in an orally available form selected from the group consisting of tablets and capsules.

5. The method as claimed in claim 1, wherein the 9-deoxy-2',9-α-methano-3-oxa-4,5,6-trinor-3,7-(1',3'-interphenylene)-13,14-dihydro-prostaglandin $F_1$ is administered by inhalation.

6. The method as claimed in claim 1, wherein the 9-deoxy-2',9-α-methano-3-oxa-4,5,6-trinor-3,7-(1',3'-interphenylene)-13,14-dihydro-prostaglandin $F_1$ is administered subcutaneously.

7. The method as claimed in claim 1, wherein the peripheral vascular disease is peripheral arterial occlusive disease.

8. The method as claimed in claim 1, wherein the peripheral vascular disease is intermittent claudication.

9. The method as claimed in claim 1, wherein the effective amount is 10 ng/kg of body weight/min.

10. A kit for treatment of peripheral vascular disease comprising (i) an effective amount of 9-deoxy-2',9-α-methano-3-oxa-4,5,6-trinor-3,7-(1',3'-interphenylene)-13,14-dihydro-prostaglandin $F_1$, its pharmaceutically acceptable salts, and/or acid derivatives thereof, (ii) one or more pharmaceutically acceptable carriers and/or additives, and (iii) instructions for use in treating peripheral vascular disease.

11. The kit as claimed in claim 10, wherein component (i) is a pharmaceutically acceptable salt of 9-deoxy-2',9-α-methano-3-oxa-4,5,6-trinor-3,7-(1',3'-interphenylene)-13,14-dihydro-prostaglandin $F_1$.

12. The kit as claimed in claim 10, wherein component (i) is 9-deoxy-2',9-α-methano-3-oxa-4,5,6-trinor-3,7-(1',3'-interphenylene)-13,14-dihydro-prostaglandin $F_1$ in an orally available form selected from the group consisting of tablets and capsules.

13. The kit as claimed in claim 10, wherein component (i) is 9-deoxy-2',9-α-methano-3-oxa-4,5,6-trinor-3,7-(1',3'-interphenylene)-13,14-dihydro-prostaglandin $F_1$ in a form suitable for inhalation.

14. The kit as claimed in claim 10, wherein component (i) is 9-deoxy-2',9-α-methano-3-oxa-4,5,6-trinor-3,7-(1',3'-interphenylene)-13,14-dihydro-prostaglandin $F_1$ in a form suitable for subcutaneous administration.

15. The kit as claimed in claim 10, wherein the peripheral vascular disease is peripheral arterial occlusive disease.

16. The kit as claimed in claim 10, wherein the peripheral vascular disease is intermittent claudication.

17. The kit as claimed in claim 10, wherein the effective amount is 10 ng/kg of body weight/min.

* * * * *

UNITED STATES PATENT AND TRADEMARK OFFICE
CERTIFICATE OF CORRECTION

PATENT NO. : 6 054 486
DATED : April 25, 2000
INVENTOR(S) : James Crow et al.

It is certified that error appears in the above-indentified patent and that said Letters Patent is hereby corrected as shown below:

Cover page, line [73] Assignee: United Technology Corporation should be --United Therapeutics Corporation--.

Signed and Sealed this

Fifteenth Day of May, 2001

Attest:

NICHOLAS P. GODICI

Attesting Officer

Acting Director of the United States Patent and Trademark Office